US012623996B2

(12) United States Patent
Yamauchi

(10) Patent No.: US 12,623,996 B2

(45) Date of Patent: May 12, 2026

(54) METHOD FOR INDUSTRIALLY PRODUCING DIALKYL CARBONATE AND DIOL

(71) Applicant: ASAHI KASEI KABUSHIKI KAISHA, Tokyo (JP)

(72) Inventor: Hironobu Yamauchi, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 555 days.

(21) Appl. No.: 18/271,084

(22) PCT Filed: Nov. 18, 2021

(86) PCT No.: PCT/JP2021/042494

§ 371 (c)(1),
(2) Date: Jul. 6, 2023

(87) PCT Pub. No.: WO2022/149357

PCT Pub. Date: Jul. 14, 2022

(65) Prior Publication Data

US 2024/0051911 A1 Feb. 15, 2024

(30) Foreign Application Priority Data

Jan. 8, 2021 (JP) ................................ 2021-002028

(51) Int. Cl.
*C07C 68/065* (2020.01)
*C07C 29/147* (2006.01)

(52) U.S. Cl.
CPC .......... *C07C 68/065* (2013.01); *C07C 29/147* (2013.01)

(58) Field of Classification Search
CPC .................................................... C07C 68/065
See application file for complete search history.

(56) References Cited

U.S. PATENT DOCUMENTS

| | | | |
|---|---|---|---|
| 2003/0078448 | A1 | 4/2003 | Buchanan et al. |
| 2008/0128949 | A1 | 6/2008 | Yokoyama et al. |
| 2009/0030223 | A1 | 1/2009 | Fukuoka et al. |
| 2009/0054676 | A1 | 2/2009 | Fukuoka et al. |
| 2009/0105494 | A1 | 4/2009 | Fukuoka et al. |
| 2009/0137833 | A1 | 5/2009 | Fukuoka et al. |

FOREIGN PATENT DOCUMENTS

| | | | |
|---|---|---|---|
| CN | 101312932 | A | 11/2008 |
| CN | 101346164 | A | 1/2009 |
| CN | 101346340 | A | 1/2009 |
| EP | 1 426 086 | A1 | 6/2004 |
| EP | 1 967 242 | A1 | 9/2008 |
| GB | 2 109 265 | A | 6/1983 |
| JP | 2000-300903 | A | 10/2000 |
| JP | 2002-371037 | A | 12/2002 |
| JP | 2003-81893 | A | 3/2003 |
| JP | 2003-300936 | A | 10/2003 |
| JP | 2003-342209 | A | 12/2003 |
| TW | 200631995 | A | 9/2006 |
| WO | WO 03/033450 | A1 | 4/2003 |
| WO | WO 2007/060894 | A1 | 5/2007 |
| WO | WO 2007/069514 | A1 | 6/2007 |

OTHER PUBLICATIONS

"Investigation and Design Certified Petroleum and Natural Gas Engineer Qualification Examination Professional Examination Review Guide," Investigation and Design Certified Engineer Petroleum and Natural Gas Professional Management Committee, China University of Petroleum Press, vol. 2, 1st Edition, Jul. 31, 2006. pp. 281-282 (6 pages total), with partial English translation.

Yangchu et al., "Fig. 9-11: Structural parameters of single-overflow valve tray," Fundamentals of Petrochemical Engineering, University of Petroleum Press, 1st Edition, Jul. 31, 1997, pp. 348-349 (5 pages total), with partial English translation.

International Preliminary Report on Patentability and English translation of the Written Opinion of the International Searching Authority for International Application No. PCT/JP2021/042494, dated Jul. 20, 2023.

International Search Report for International Application No. PCT/JP2021/042494, dated Jan. 11, 2022, with English translation.

Supplementary European Search Report for European Application No. 21917582.5, dated Mar. 13, 2024.

*Primary Examiner* — Paul V Ward

(74) *Attorney, Agent, or Firm* — Birch, Stewart, Kolasch & Birch, LLP

(57) ABSTRACT

The method for industrially producing a dialkyl carbonate and a diol, in which the dialkyl carbonate and the diol are continuously produced through a reactive distillation system of taking a cyclic carbonate and an aliphatic monohydric alcohol as starting materials, comprising the steps of: continuously feeding the starting materials into a continuous multi-stage distillation column in which a homogeneous catalyst is present; carrying out reaction and distillation simultaneously in the column; continuously withdrawing a low boiling point reaction mixture containing the produced dialkyl carbonate in a gaseous form from an upper portion of the column; and continuously withdrawing a high boiling point reaction mixture containing the diol in a liquid form from a lower portion of the column, where the method satisfies specific requirements.

9 Claims, 2 Drawing Sheets

[Figure 1]
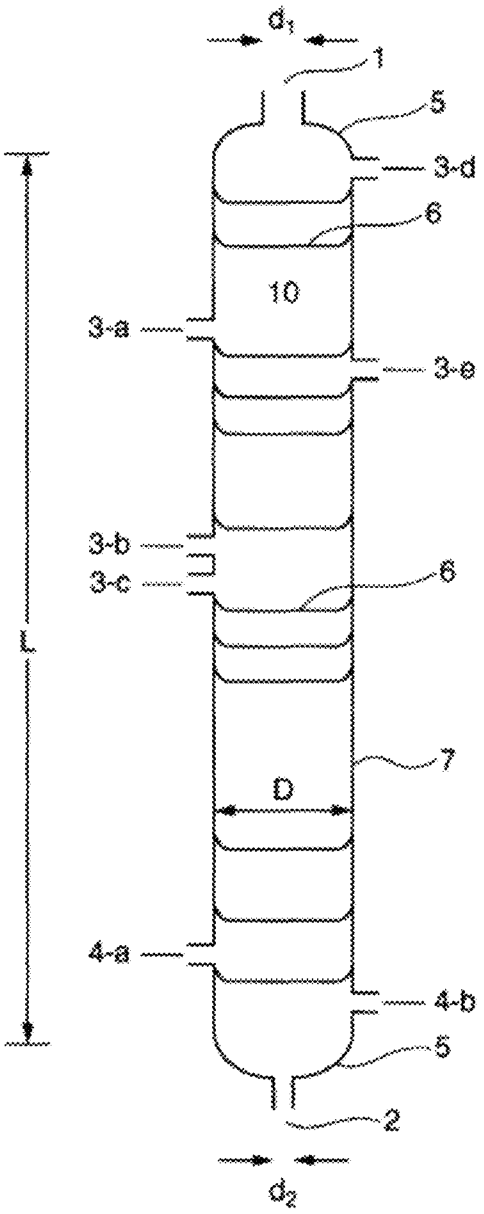

[Figure 2]
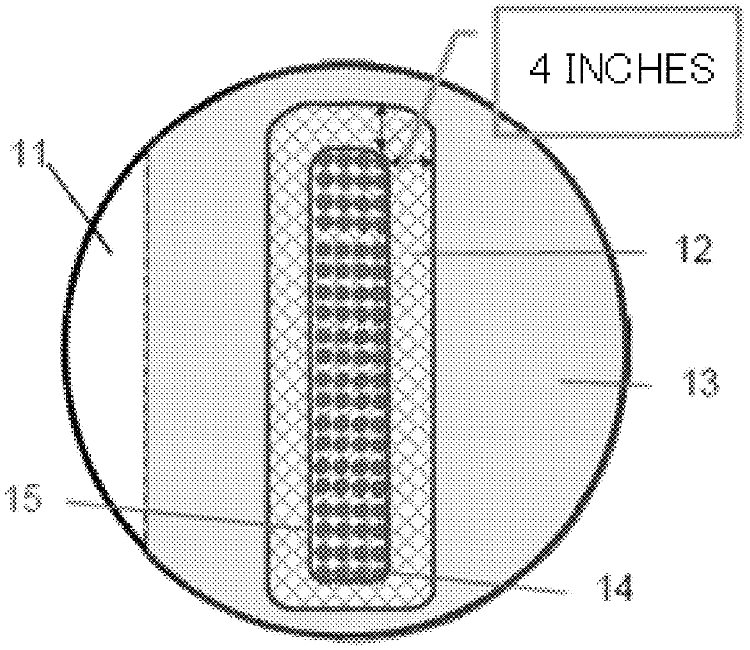

METHOD FOR INDUSTRIALLY PRODUCING DIALKYL CARBONATE AND DIOL

TECHNICAL FIELD

The present invention relates to a method for industrially producing a dialkyl carbonate and a diol.

BACKGROUND ART

As a method for industrially producing a dialkyl carbonate and a diol, for example, Patent Document 1 proposes a method and an apparatus for producing a dialkyl carbonate and a diol in industrially large quantities (e.g., 2 tons or more of dialkyl carbonate per hour and 1.3 tons or more of diol per hour) through a reactive distillation system of taking a cyclic carbonate and an aliphatic monohydric alcohol as starting materials, comprising continuously feeding the starting materials into a continuous multi-stage distillation column in which a homogeneous catalyst is present, and carrying out reaction and distillation simultaneously in the column, where they can be produced stably in a high yield for a prolonged period (e.g., 5,000 hours or more) with high selectivity and high productivity.

LIST OF PRIOR ART DOCUMENTS

Patent Document

Patent Document 1: International Publication No. WO 2007/069514

SUMMARY OF INVENTION

Problems to be Solved by Invention

However, the method and apparatus described in Patent Document 1 sometimes don't have sufficient productivity of a dialkyl carbonate and a diol relative to the size of the apparatus.

Accordingly, the problem to be solved by the present invention is to provide a specific method for industrially producing a dialkyl carbonate and a diol in industrially large quantities through a reactive distillation system of taking a cyclic carbonate and an aliphatic monohydric alcohol as starting materials, comprising continuously feeding the starting materials into a continuous multi-stage distillation column in which a homogeneous catalyst is present, and carrying out reaction and distillation simultaneously in the column, where they can be produced with stable and even higher productivity (for example, 4.5 tons or more of dialkyl carbonate per hour and 2.7 tons or more of diol per hour) for a prolonged period (for example, 1,000 hours or more, preferably 3,000 hours or more, more preferably 5,000 hours or more) with stable high selectivity and high yield.

Means for Solving Problems

The present inventors have carried out intensive studies to solve the above-mentioned problems, and have found that, in producing a dialkyl carbonate and a diol in industrially large quantities with a column in the same length and inner diameter, by setting the length and inner diameter of the column, and the active area and the open area percentages of each stage tray in the column to a specific range, the dialkyl carbonate and the diol can be produced with stable and even higher productivity [e.g., 1.3 times or more (i.e., 4.5 tons or more of dialkyl carbonate per hour and 2.7 tons or more of diol per hour) the target value described in Patent Document 1 (2 tons or more of dialkyl carbonate per hour and 1.3 tons or more of diol per hour)] for a prolonged period (e.g., 1,000 hours or more, preferably 3,000 hours or more, and more preferably 5,000 hours or more) with stable high selectivity and high yield. As a result, the present inventors have arrived at the present invention. That is, the present invention is as follows.

[1]

A method for industrially producing a dialkyl carbonate and a diol in which the dialkyl carbonate and the diol are continuously produced through a reactive distillation system of taking a cyclic carbonate and an aliphatic monohydric alcohol as starting materials, comprising:

continuously feeding the starting materials into a continuous multi-stage distillation column in which a homogeneous catalyst is present;

carrying out reaction and distillation simultaneously in the column;

continuously withdrawing a low boiling point reaction mixture containing the produced dialkyl carbonate in a gaseous form from an upper portion of the column; and continuously withdrawing a high boiling point reaction mixture containing the diol in a liquid form from a lower portion of the column, wherein:

(a) the continuous multi-stage distillation column comprises a tray column type distillation column which has a structure having a cylindrical trunk portion having a length L (cm) and an inner diameter D (cm) and having an internal therein, the internal being a tray having a plurality of holes, and the column further has a gas outlet at a column top portion or in the upper portion of the column near to the column top portion, a liquid outlet at a column bottom portion or in the lower portion of the column near to the column bottom portion, one or more first inlets provided in the upper portion and/or a middle portion of the column below the gas outlet, and one or more second inlets provided in the middle portion and/or the lower portion of the column above the liquid outlet, wherein:

(1) the length L (cm) of the column satisfies Formula (1):

$$1{,}500 \le L \le 12{,}000; \quad (1)$$

(2) the inner diameter D (cm) of the column satisfies Formula (2):

$$120 \le D \le 3{,}000;$$

(3) the internal consists of three types of trays of upper, middle, and lower stages;

(4) the starting material cyclic carbonate is continuously introduced into the continuous multi-stage distillation column through the one or more first inlets, and the upper stage is a stage above a stage of the inlet of an uppermost stage among the one or more first inlets, and a percentage of the number of trays of the upper stage is 1 to 10% of the total number of stages, (5) the starting material aliphatic monohydric alcohol is continuously introduced into the continuous multi-stage distillation column through the one or more second inlets, and the middle stage is a stage from a stage of the inlet of an uppermost stage among the one or more second inlets to the stage of the inlet of the uppermost stage among the one or more first inlets, and a percentage of the number of trays of the middle stage is 40 to 50% of the total number of stages;

(6) the lower stage is a stage below the stage of the inlet of the uppermost stage among the one or more second inlets, and a percentage of the number of trays of the lower stage is 45 to 55% of the total number of stages;

(7) in each stage tray of the lower stage, a percentage of active area calculated by Formula (i) below is 40 to 80%, and a percentage of open area calculated by Formula (ii) below is 1.0 to 5.0%:

$$\text{Percentage (\%) of active area} = \text{area (cm}^2\text{) of active area/area (cm}^2\text{) of tray} \times 100 \quad \text{(i)}$$

wherein the area of active area is an area of a compartment with a hole in a tray deck portion (ranging from a boundary of a minimum segment including all holes to 4 inches further outward), and the area of tray is an area of the tray deck portion, including the area of active area, but not including a downcomer portion;

$$\text{Percentage (\%) of open area} = \text{area (cm}^2\text{) of open area/area (cm}^2\text{) of active area} \times 100 \quad \text{(ii)}$$

wherein the area of open area is the total area of all holes in the active area, and the area of active area is as defined in Formula (i);

(8) in each stage tray of the upper and middle stages, the percentage of active area calculated by Formula (i) above is 40 to 80%, and the percentage of open area calculated by Formula (ii) above is 1.0 times or more the percentage of open area calculated by Formula (ii) above in each stage tray of the lower stage; and (9) the homogeneous catalyst consists of a mixture of an alkali metal and ethylene glycol, and a mass ratio of the alkali metal to the ethylene glycol (alkali metal/ethylene glycol) in the homogeneous catalyst is 0.05 to 0.5, and a catalyst concentration (in terms of alkali metal concentration) is 0.05 to 2.0% by mass of the cyclic carbonate fed to the distillation column.

[2]

The method according to [1], wherein in the upper stage, a gas flow rate is 5,000 to 45,000 kg/hr, and a liquid flow rate is 1,000 to 15,000 kg/hr, in the middle stage, the gas flow rate is 5,000 to 30,000 kg/hr, and the liquid flow rate is 1,000 to 15,000 kg/hr, and in the lower stage, the gas flow rate is 5,000 to 20,000 kg/hr, and the liquid flow rate is 1,000 to 30,000 kg/hr.

[3]

The method according to [1] or [2], wherein an amount of the dialkyl carbonate produced is 4.5 tons or more per hour.

[4]

The method according to any of [1] to [3], wherein an amount of the diol produced is 2.5 tons or more per hour.

[5]

A continuous multi-stage distillation column for carrying out transesterification reaction between a cyclic carbonate and an aliphatic monohydric alcohol and distillation, wherein (a) the continuous multi-stage distillation column comprises:

a cylindrical trunk portion having a length L (cm) and an inner diameter D (cm);

a tray having a plurality of holes, provided inside the trunk portion as an internal;

a gas outlet provided at a column top portion or in an upper portion of the column near to the column top portion;

a liquid outlet provided at a column bottom portion or in a lower portion of the column near to the column bottom portion;

one or more first inlets provided in the upper portion and/or a middle portion of the column below the gas outlet; and one or more second inlets provided in the middle portion and/or the lower portion of the column above the liquid outlet;

(1) the length L (cm) of the column satisfies Formula (1):

$$1{,}500 \le L \le 12{,}000; \quad (1)$$

(2) the inner diameter D (cm) of the column satisfies Formula (2):

$$120 \le D \le 3{,}000; \quad (2)$$

(3) the internal consists of three types of trays of upper, middle, and lower stages;

(4) the starting material cyclic carbonate is continuously introduced into the continuous multi-stage distillation column through the one or more first inlets, and the upper stage is a stage above a stage of the inlet of an uppermost stage among the one or more first inlets, and a percentage of the number of trays of the upper stage is 1 to 10% of the total number of stages, (5) the starting material aliphatic monohydric alcohol is continuously introduced into the continuous multi-stage distillation column through the one or more second inlets, and the middle stage is a stage from a stage of the inlet of an uppermost stage among the one or more second inlets to the stage of the inlet of the uppermost stage among the one or more first inlets, and a percentage of the number of trays of the middle stage is 40 to 50% of the total number of stages;

(6) the lower stage is a stage below the stage of the inlet of the uppermost stage among the one or more second inlets, and a percentage of the number of trays of the lower stage is 45 to 55% of the total number of stages;

(7) in each stage tray of the lower stage, a percentage of active area calculated by Formula (i) below is 40 to 80%, and a percentage of open area calculated by Formula (ii) below is 1.0 to 5.0%:

$$\text{Percentage (\%) of active area} = \text{area (cm}^2\text{) of active area/area (cm}^2\text{) of tray} \times 100 \quad \text{(i)}$$

wherein the area of active area is an area of a compartment with a hole in a tray deck portion (ranging from a boundary of a minimum segment including all holes to 4 inches further outward), and the area of tray is an area of the tray deck portion, including the area of active area, but not including a downcomer portion;

$$\text{Percentage (\%) of open area} = \text{area (cm}^2\text{) of open area/area (cm}^2\text{) of active area} \times 100 \quad \text{(ii)}$$

wherein the area of open area is the total area of all holes in the active area, and the area of active area is as defined in Formula (i); and (8) in each stage tray of the upper and middle stages, the percentage of active area calculated by Formula (i) above is 40 to 80%, and the percentage of open area calculated by Formula (ii) above is 1.0 times or more the percentage of open area calculated by Formula (ii) above in each stage tray of the lower stage.

Advantages of Invention

According to the present invention, in producing a dialkyl carbonate and a diol in industrially large quantities with a column in the same length and inner diameter, the dialkyl carbonate and the diol can be produced with stable and even higher productivity [e.g., 1.3 times or more (i.e., 4.5 tons or more of dialkyl carbonate per hour and 2.7 tons or more of diol per hour) the target value described in Patent Document 1 (2 tons or more of dialkyl carbonate per hour and 1.3 tons or more of diol per hour)] for a prolonged period (e.g., 1,000 hours or more, preferably 3,000 hours or more, and more preferably 5,000 hours or more) with stable high selectivity and high yield.

BRIEF DESCRIPTION OF DRAWINGS

FIG. 1 is a diagram illustrating an example of a production apparatus used for producing a dialkyl carbonate and a diol of the present invention.

FIG. 2 is a conceptual diagram of an example of a tray structure in a continuous multi-stage distillation column used in the present invention.

MODE FOR CARRYING OUT INVENTION

Hereinafter, an embodiment for carrying out the present invention (hereinafter referred to as the "present embodiment") will be described in more detail, but the present invention is not limited thereto, and various variations can be made without departing from the gist thereof.

A method for industrially producing a dialkyl carbonate and a diol of the present embodiment is a method in which the dialkyl carbonate and the diol are continuously produced through a reactive distillation system of taking a cyclic carbonate and an aliphatic monohydric alcohol as starting materials, comprising:

continuously feeding the starting materials into a continuous multi-stage distillation column in which a homogeneous catalyst is present;

carrying out reaction and distillation simultaneously in the column;

continuously withdrawing a low boiling point reaction mixture containing the produced dialkyl carbonate in a gaseous form from an upper portion of the column; and continuously withdrawing a high boiling point reaction mixture containing the diol in a liquid form from a lower portion of the column, wherein:

(a) the continuous multi-stage distillation column comprises a tray column type distillation column which has a structure having a cylindrical trunk portion having a length L (cm) and an inner diameter D (cm) and having an internal therein, the internal being a tray having a plurality of holes, and the column further has a gas outlet at a column top portion or in the upper portion of the column near to the column top portion, a liquid outlet at a column bottom portion or in the lower portion of the column near to the column bottom portion, one or more first inlets provided in the upper portion and/or a middle portion of the column below the gas outlet, and one or more second inlets provided in the middle portion and/or the lower portion of the column above the liquid outlet, wherein:

(1) the length L (cm) of the column satisfies Formula (1):

$$1{,}500 \leq L \leq 12{,}000; \quad (1)$$

(2) the inner diameter D (cm) of the column satisfies Formula (2):

$$120 \leq D \leq 3{,}000; \quad (2)$$

(3) the internal consists of three types of trays of upper, middle, and lower stages;

(4) the starting material cyclic carbonate is continuously introduced into the continuous multi-stage distillation column through the one or more first inlets, and the upper stage is a stage above a stage of the inlet of the uppermost stage among the one or more first inlets, and a percentage of the number of trays of the upper stage is 1 to 10% of the total number of stages, (5) the starting material aliphatic monohydric alcohol is continuously introduced into the continuous multi-stage distillation column through the one or more second inlets, and the middle stage is a stage from a stage of the inlet of the uppermost stage among the one or more second inlets to the stage of the inlet of the uppermost stage among the one or more first inlets, and a percentage of the number of trays of the middle stage is 40 to 50% of the total number of stages;

(6) the lower stage is a stage below the stage of the inlet of the uppermost stage among the one or more second inlets, and a percentage of the number of trays of the lower stage is 45 to 55% of the total number of stages;

(7) in each stage tray of the lower stage, a percentage of active area calculated by Formula (i) below is 40 to 80%, and a percentage of open area calculated by Formula (ii) below is 1.0 to 5.0%:

$$\text{Percentage (\%) of active area} = \text{area (cm}^2\text{) of active area/area (cm}^2\text{) of tray} \times 100 \quad \text{(i)}$$

wherein the area of active area is an area of a compartment with a hole in a tray deck portion (ranging from a boundary of a minimum segment including all holes to 4 inches further outward), and the area of tray is an area of the tray deck portion, including the area of active area, but not including a downcomer portion;

$$\text{Percentage (\%) of open area} = \text{area (cm}^2\text{) of open area/area (cm}^2\text{) of active area} \times 100 \quad \text{(ii)}$$

wherein the area of open area is the total area of all holes in the active area, and the area of active area is as defined in Formula (i);

(8) in each stage tray of the upper and middle stages, the percentage of active area calculated by Formula (i) above is 40 to 80%, and the percentage of open area calculated by Formula (ii) above is 1.0 times or more the percentage of open area calculated by Formula (ii) above in each stage tray of the lower stage; and (9) the homogeneous catalyst consists of a mixture of an alkali metal and ethylene glycol, and a mass ratio of the alkali metal to the ethylene glycol (alkali metal/ethylene glycol) in the homogeneous catalyst is 0.05 to 0.5, and a catalyst concentration (in terms of alkali metal concentration) is 0.05 to 2.0% by mass of the cyclic carbonate fed to the distillation column.

The production method of the present embodiment, by employing the configurations described above, enables a dialkyl carbonate and a diol to be industrially produced with stable and even higher productivity (e.g., 4.5 tons or more of dialkyl carbonate per hour and 2.7 tons or more of diol per hour) for a prolonged period (e.g., 1,000 hours or more, preferably 3,000 hours or more, more preferably 5,000 hours or more) with stable high selectivity and high yield.

The reaction used in the production method of the present embodiment is a reversible equilibrium transesterification reaction represented by Chemical Formula below in which a dialkyl carbonate (C) and a diol (D) are produced from a cyclic carbonate (A) and an aliphatic monohydric alcohol (B).

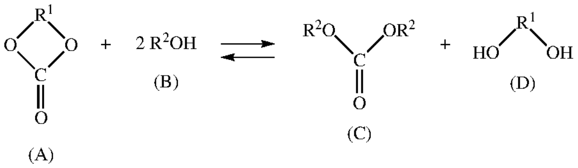

(A) (B) (C) (D)

Wherein $R^1$ represents a bivalent group $-(CH_2)_m-$ (m is an integer from 2 to 6), and one or more hydrogens thereof are optionally substituted with an alkyl group having 1 to 10 carbon atoms or an aryl group. $R^2$ represents a monovalent aliphatic group having 1 to 12 carbon atoms, and one or more hydrogens thereof are optionally substituted with an alkyl group having 1 to 10 carbon atoms or an aryl group.

The cyclic carbonate used as a starting material in the production method of the present embodiment is a compound represented by (A) in Chemical Formula above. Examples of the cyclic carbonate preferably used include alkylene carbonates such as ethylene carbonate or propylene carbonate, 1,3-dioxacyclohexa-2-one, and 1,3-dioxacyclohepta-2-one. The ethylene carbonate or propylene carbonate is more preferably used due to ease of procurement and the like, and the ethylene carbonate is particularly preferably used.

The aliphatic monohydric alcohol used as the other starting material is a compound represented by (B) in Chemical Formula above. It is preferable to use an aliphatic monohydric alcohol having a lower boiling point than that of the diol produced. Although possibly varying depending on the type of the cyclic carbonate used, examples of the aliphatic monohydric alcohol include methanol, ethanol, propanol (isomers), allyl alcohol, butanol (isomers), 3-buten-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers), and the like. Furthermore, these aliphatic monohydric alcohols may be substituted with substituents such as halogens, lower alkoxy groups, cyano groups, alkoxycarbonyl groups, aryloxycarbonyl groups, acyloxy groups, and nitro groups.

Of such aliphatic monohydric alcohols, ones preferably used are alcohols having 1 to 6 carbon atoms, more preferably alcohols having 1 to 4 carbon atoms, i.e., methanol, ethanol, propanol (isomers), and butanol (isomers). In the case of using the ethylene carbonate or propylene carbonate as the cyclic carbonate, preferable aliphatic monohydric alcohols are methanol and ethanol, particularly methanol.

In the production method of the present embodiment, the starting material cyclic carbonate is continuously introduced into the continuous multi-stage distillation column through one or more first inlets, and the starting material aliphatic monohydric alcohol is continuously introduced into the continuous multi-stage distillation column through one or more second inlets. By continuously introducing each starting material from such a position to the continuous multi-stage distillation column, an optimal reaction efficiency of a dialkyl carbonate and a diol can be achieved to ensure an adequate amount produced, and an optimal separation performance can be achieved to fully ensure the dialkyl carbonate and the diol.

In the production method of the present embodiment, the homogeneous catalyst is made to be present in the reactive distillation column. The method of making the homogeneous catalyst to be present may be any method, but it is preferable to continuously feed the catalyst into the reactive distillation column to make the catalyst present in a liquid phase in the reactive distillation column.

In the case where the homogeneous catalyst is continuously fed into the reactive distillation column, the homogeneous catalyst may be fed together with the cyclic carbonate and/or the aliphatic monohydric alcohol, or may be fed at a position different from those for the starting materials. The reaction actually proceeds in the distillation column in a region below the position at which the catalyst is fed, and hence it is preferable to feed the catalyst into a region between the top of the column and the position(s) at which the starting materials are fed. The catalyst is preferably present in 5 stages or more, more preferably 7 stages or more, and further preferably 10 stages or more.

The catalyst used in the production method of the present embodiment is a compound consisting of a mixture of alkali metal and ethylene glycol. The mass ratio of the alkali metal to ethylene glycol (alkali metal/ethylene glycol) in the homogeneous catalyst is preferably 0.05 to 0.5, more preferably 0.1 to 0.4, and further preferably 0.2 to 0.3. When the mass ratio of alkali metal to ethylene glycol (alkali metal/ethylene glycol) is in the above range, the production of a dialkyl carbonate and a diol can be promoted and the production of impurities can be suppressed. The catalyst concentration (in terms of alkali metal concentration) is 0.05 to 2.0% by mass to the cyclic carbonate (e.g., ethylene carbonate (EC)) fed to the distillation column.

Examples of the alkali metal in the catalyst used in the production method of the present embodiment include, but are not particularly limited to, lithium, potassium, sodium, and cesium, preferably potassium and sodium.

The amount of the catalyst (in terms of alkali metal concentration) used in the production method of the present embodiment is usually a ratio of 0.05 to 2.0% by mass, preferably 0.1 to 1.0% by mass, further preferably 0.5 to 1.0% by mass, to the mass of the starting material cyclic carbonate fed.

When the amount of the catalyst is not less than the lower limit value, the reaction and yield become sufficient, and the amount produced is increased. When the amount of the catalyst is not more than the upper limit value, the impurities (high boiling point components) are suppressed, and the product purity is improved. In addition, it is possible to suppress the withdrawal of part of the catalyst to the outside of the system with impurities (high boiling point components), thereby reducing the loss of the catalyst.

When continuously feeding the cyclic carbonate into the continuous multi-stage distillation column (e.g., having the number of stages n) that is the reactive distillation column in the production method of the present embodiment, it is preferable for the cyclic carbonate to be fed into a specified stage. For example, it is preferable that the starting material cyclic carbonate is continuously introduced into the continuous multi-stage distillation column through one or more inlets provided between the 3rd stage from the top of the continuous multi-stage distillation column and the (n/3)th stage from the top of the continuous multi-stage distillation column. It is preferable in the stages above the inlet(s) of cyclic carbonate that high boiling point compounds such as the cyclic carbonate and the diols are not contained in the components at the top of the column. For this, there are preferably 3 stages or more, more preferably 4 to 10 stages, further preferably 5 to 8 stages, above the inlet(s) of cyclic carbonate.

In the production method of the present embodiment, the internal in the continuous multi-stage distillation column consists of three types of trays of upper stage, middle stage, and lower stage.

The upper stage is a stage above a stage of the inlet of the uppermost stage among the one or more first inlets. The middle stage is a stage from a stage of the inlet of the uppermost stage among the one or more second inlets to the stage of the inlet of the uppermost stage among the one or more first inlets. The lower stage is a stage below the stage of the inlet of the uppermost stage among the one or more second inlets.

In the production method of the present embodiment, the number of stages n, which is the total number of stages of the upper, middle, and lower stages, is preferably 10 to 100 stages, more preferably 30 to 100 stages, and further preferably 30 to 80 stages.

In the production method of the present embodiment, the percentage of the number of trays of the upper stage is 1 to 10% of the total number of stages, preferably 3 to 10%, and more preferably 5 to 10%. The percentage of the number of trays of the middle stage is 40 to 50% of the total number of stages, preferably 40 to 45%, and more preferably 40 to 43%. The percentage of the number of trays of the lower stage is 45 to 55% of the total number of stages, preferably 48 to 55%, and more preferably 50 to 55%. When the percentage of the upper, middle, and lower stages is taken as the above range, an optimal reaction efficiency of a dialkyl carbonate and a diol can be achieved to ensure an adequate amount produced, and an optimal separation performance can be achieved to fully ensure the dialkyl carbonate and the diol.

The cyclic carbonate preferably used in the present embodiment is a cyclic carbonate not containing a halogen, where the cyclic carbonate is produced through a reaction between, for example, an alkylene oxide such as ethylene oxide, propylene oxide or styrene oxide, and carbon dioxide. A cyclic carbonate containing small amounts of these starting material compounds, diols, or the like may thus be used as the starting material in the present embodiment. The cyclic carbonate may be derived from a biomass. Examples of such cyclic carbonates include a cyclic carbonate obtained from bioethanol that is a starting material.

In the present embodiment, the starting material aliphatic monohydric alcohol may be a high-purity aliphatic monohydric alcohol, or may contain other compounds. Specifically, for example, it is preferable to use an aliphatic monohydric alcohol containing dialkyl carbonates at 1 to 15% by mass, more preferably an aliphatic monohydric alcohol containing dialkyl carbonates at 1.5 to 12% by mass, and further preferably an aliphatic monohydric alcohol containing dialkyl carbonates at 2 to 10% by mass, based on the total mass of the aliphatic monohydric alcohol and the dialkyl carbonates.

When industrially carrying out the present reaction, it is preferable that, besides fresh cyclic carbonate and/or aliphatic monohydric alcohol that are newly introduced into the reaction system, a material containing the cyclic carbonate and/or the aliphatic monohydric alcohol as a main component, which is recovered from this process and/or another process, can also be used for the starting materials. The production method of the present embodiment makes this possible, and this is one of the excellent features of the production method of the present embodiment. Examples of the another process include a process of producing a diaryl carbonate from a dialkyl carbonate and an aromatic monohydroxy compound. In this process, aliphatic monohydric alcohols are by-produced and recovered. The recovered by-produced aliphatic monohydric alcohols generally contain the dialkyl carbonate. When the content of the dialkyl carbonate is in the range described above, excellent effects of the production method of the present embodiment can be further exhibited. The recovered by-produced aliphatic monohydric alcohols may further contain an aromatic monohydroxy compound, an alkyl aryl ether, small amounts of an alkyl aryl carbonate and the diaryl carbonate, and the like. In the production method of the present embodiment, the by-produced aliphatic monohydric alcohol may be used as is as a starting material, or may be used as the starting material after the amount of contained material having a higher boiling point than that of the aliphatic monohydric alcohol has been reduced through distillation or the like.

When continuously feeding the aliphatic monohydric alcohol into the continuous multi-stage distillation column (e.g., having the number of stages n) that is the reactive distillation column in the production method of the present embodiment, it is preferable for the aliphatic monohydric alcohol to be fed into a specified stage. For example, in the production method of the present embodiment, it is preferable that the starting material aliphatic monohydric alcohol is continuously introduced into the continuous multi-stage distillation column through one or more inlets provided between the (n/3)th stage from the top of the continuous multi-stage distillation column and the (2n/3)th stage from the top of the continuous multi-stage distillation column. When the aliphatic monohydric alcohol used as the starting material in the production method of the present embodiment contains a specific amount of dialkyl carbonate, the excellent effects of the production method of the present embodiment can be further exhibited by setting the inlet to a specific stage. More preferably, the aliphatic monohydric alcohol is continuously introduced into the continuous multi-stage distillation column through one or more inlets provided between the (2n/5)th stage from the top of the continuous multi-stage distillation column and the (3n/5)th stage from the top of the continuous multi-stage distillation column.

It is preferable that the starting materials are fed continuously into the distillation column in a liquid form, in a gaseous form, or as a mixture of a liquid and a gas. Other than feeding the starting materials into the distillation column in this way, it is also preferable to additionally feed a gaseous starting material intermittently or continuously thereto from the middle portion and/or the lower portion of the distillation column. Moreover, another preferable method is one in which the cyclic carbonate is continuously fed into the distillation column in a liquid form or a gas/liquid mixed form through one or more inlets provided in a stage of the distillation column above the stages in which the catalyst is present, and the aliphatic monohydric alcohol is continuously fed into the distillation column in a gaseous form and/or a liquid form through one or more inlets provided in the stage of the distillation column as described above. The starting materials are preferably brought into contact with the catalyst in a region of at least 5 stages or more, preferably 7 stages or more, more preferably 10 stages or more, of the distillation column.

In the production method of the present embodiment, a ratio between the amounts of the cyclic carbonate and the aliphatic monohydric alcohol fed into the reactive distillation column varies according to the type and amount of the transesterification catalyst and the reaction conditions, but preferably, the aliphatic monohydric alcohols can be fed in the range of 0.01 to 1,000 times in molar ratio relative to the cyclic carbonate fed. To increase the reactivity of the cyclic carbonate, it is preferable to feed an excessive amount of the aliphatic monohydric alcohol of at least 2 times the mols of the cyclic carbonate, but if the amount of the aliphatic monohydric alcohol used is too excessive, it may be necessary to make the apparatus larger. For this, the molar ratio of the aliphatic monohydric alcohol to the cyclic carbonate is preferably from 2 to 20, more preferably from 3 to 15, yet more preferably from 5 to 12. Furthermore, if much unreacted cyclic carbonate remains, then the unreacted cyclic carbonate may react with the product diol to by-produce multimers such as a dimer or a trimer, and hence in industrial implementation, it is preferable to reduce the remaining amount of unreacted cyclic carbonate as much as possible. In the production method of the present embodiment, even if the molar ratio is not more than 10, the reactivity of the cyclic carbonate can be made to be 98% or more, preferably 99% or more, and further preferably 99.9% or more. This is another characteristic feature of the production method of the present embodiment.

In the production method of the present embodiment, it is preferably possible to continuously produce 4.5 tons or more of dialkyl carbonate per hour, and the minimum amount of the cyclic carbonate continuously fed to achieve this, based on the amount of the dialkyl carbonate to be produced (p ton/hr), is generally 2.0 p ton/hr, preferably 1.5 p ton/hr, and more preferably 1.3 p ton/hr. In a yet more preferable case, this amount can be made to be less than 1.0 p ton/hr.

FIG. 1 is a schematic diagram illustrating an example of the continuous multi-stage distillation column used in the production method according to the present embodiment. Here, the continuous multi-stage distillation column 10 used in the production method of the present embodiment comprises a tray column type distillation column which has a structure having end plates 5 respectively above and below a cylindrical trunk portion 7 having a length L (cm) and an inner diameter D (cm), and having an internal with n stages therein, the internal being a tray having a plurality of holes, and which further has a gas outlet 1 having an inner diameter $d_1$ (cm) at the column top portion or in an upper portion of the column near to the column top portion, a liquid outlet 2 having an inner diameter $d_2$ (cm) at the column bottom portion or in a lower portion of the column near to the column bottom portion, one or more first inlets 3 (a, e) provided below the gas outlet 1 between the 3rd stage from the top of the continuous multi-stage distillation column and the (n/3)th stage from the top of the continuous multi-stage distillation column, and one or more second inlets 3 (*b, c*) and 4 (*a, b*) provided above the liquid outlet 2 between the (n/3)th stage from the top of the continuous multi-stage distillation column and the (2n/3)th stage from the top of the continuous multi-stage distillation column, and moreover preferably be made to satisfy various conditions so as to be able to carry out not only distillation but also reaction at the same time so as to be able to produce preferably 4.5 tons or more of dialkyl carbonate per hour and/or preferably 2.5 tons or more of diol per hour stably for a prolonged period. Note that FIG. 1 is merely one embodiment of the continuous multi-stage distillation column used in the production method of the present embodiment, and hence the arrangement of the tray stages is not limited to that shown in FIG. 1.

The continuous multi-stage distillation column according to the present embodiment satisfies conditions not only from the perspective of the distillation function, but rather combined with conditions required to make the reaction proceed stably with high reactivity and high selectivity. Specifically, the continuous multi-stage distillation column of the present embodiment is a continuous multi-stage distillation column for carrying out transesterification reaction between a cyclic carbonate and an aliphatic monohydric alcohol and distillation, wherein (a) the continuous multi-stage distillation column comprises:

a cylindrical trunk portion having a length L (cm) and an inner diameter D (cm);

a tray having a plurality of holes, provided inside the trunk portion as an internal;

a gas outlet provided at a column top portion or in an upper portion of the column near to the column top portion;

a liquid outlet provided at a column bottom portion or in a lower portion of the column near to the column bottom portion;

one or more first inlets provided in the upper portion and/or a middle portion of the column below the gas outlet; and one or more second inlets provided in the middle portion and/or the lower portion of the column above the liquid outlet;

(1) the length L (cm) of the column satisfies Formula (1):

$$1{,}500 \leq L \leq 12{,}000; \quad (1)$$

(2) the inner diameter D (cm) of the column satisfies Formula (2):

$$120 \leq D \leq 3{,}000; \quad (2)$$

(3) the internal consists of three types of trays of upper, middle, and lower stages;

(4) the starting material cyclic carbonate is continuously introduced into the continuous multi-stage distillation column through the one or more first inlets, and the upper stage is a stage above a stage of the inlet of the uppermost stage among the one or more first inlets, and a percentage of the number of trays of the upper stage is 1 to 10% of the total number of stages, (5) the starting material aliphatic monohydric alcohol is continuously introduced into the continuous multi-stage distillation column through the one or more second inlets, and the middle stage is a stage from a stage of the inlet of the uppermost stage among the one or more second inlets to the stage of the inlet of the uppermost stage among the one or more first inlets, and a percentage of the number of trays of the middle stage is 40 to 50% of the total number of stages;

(6) the lower stage is a stage below the stage of the inlet of the uppermost stage among the one or more second inlets, and a percentage of the number of trays of the lower stage is 45 to 55% of the total number of stages;

(7) in each stage tray of the lower stage, a percentage of active area calculated by Formula (i) below is 40 to 80%, and a percentage of open area calculated by Formula (ii) below is 1.0 to 5.0%:

$$\text{Percentage (\%) of active area} = \text{area (cm}^2\text{) of active area/area (cm}^2\text{) of tray} \times 100 \quad (i)$$

wherein the area of active area is an area of a compartment with a hole in a tray deck portion (ranging from a boundary of a minimum segment including all holes to 4 inches further outward), and the area of tray is an area of the tray deck portion, including the area of active area, but not including a downcomer portion;

$$\text{Percentage (\%) of open area} = \text{area (cm}^2\text{) of open area/area (cm}^2\text{) of active area} \times 100 \quad (ii)$$

wherein the area of open area is the total area of all holes in the active area, and the area of active area is as defined in Formula (i); and (8) in each stage tray of the upper and middle stages, the percentage of active area calculated by Formula (i) above is 40 to 80%, and the percentage of open area calculated by Formula (ii) above is 1.0 times or more the percentage of open area calculated by Formula (ii) above in each stage tray of the lower stage.

Note that the above requirements (1) to (8) in the continuous multi-stage distillation column of the present embodiment are the same as the requirements (1) to (8) in the production method of the present embodiment.

In the production method of the present embodiment, the gas flow rate is preferably 5,000 to 45,000 kg/hr, and the liquid flow rate is preferably 1,000 to 15,000 kg/hr in the upper stage.

In the production method of the present embodiment, the gas flow rate is preferably 5,000 to 30,000 kg/hr, and the liquid flow rate is preferably 1,000 to 15,000 kg/hr in the middle stage.

In the production method of the present embodiment, the gas flow rate is preferably 5,000 to 20,000 kg/hr, and the liquid flow rate is preferably 1,000 to 30,000 kg/hr in the lower stage.

It is preferred in the production method of the present embodiment that the dialkyl carbonates are produced at 4.5 tons or more per hour.

It is also preferred in the production method of the present embodiment that the diols are produced at 2.5 tons or more per hour.

Note that the term "a column top portion or in an upper portion of the column near to the column top portion" used in the present embodiment means the portion from the column top portion downward as far as approximately 0.25 L, and the term "a column bottom portion or in a lower portion of the column near to the column bottom portion" means the portion from the column bottom portion upward as far as approximately 0.25 L. Here, "L" is as defined above.

The production method of the present embodiment is a reactive distillation method that carries out not only distillation but also reaction at the same time, and achieves high reactivity and high selectivity (high yield); to achieve this, it has been found that it is important for achieving this to set, in addition to Formulas (1) and (2) above, the stage of the inlet of each starting material, and the active area and the open area of each tray to a specific range. Preferable ranges for the respective factors are described below.

When the L (cm) is 1,500 or more, the target amount to be produced can be achieved because the reactivity is improved, and when the L (cm) is 12,000 or less, the equipment cost can be reduced while ensuring the reactivity that can achieve the target amount to be produced. The preferred range of L (cm) is $2{,}000 \leq L \leq 10{,}000$, more preferably $2{,}200 \leq L \leq 5{,}000$, and further preferably $2{,}500 \leq L \leq 5{,}000$.

Furthermore, when the D (cm) is 120 or more, the target amount to be produced can be achieved, and when the D (cm) is 3,000 or less, the equipment cost can be reduced while achieving the target amount to be produced. The preferred range of D (cm) is $150 \le D \le 2{,}000$, more preferably $180 \le D \le 1{,}200$, further preferably $210 \le D \le 800$.

The continuous multi-stage distillation column used in the present embodiment is preferably a tray column type distillation column including n trays having a plurality of holes as the internal. The term internal used in the present embodiment means the parts in the distillation column where gas and liquid are actually brought into contact with one another. Examples of such a tray include a bubble-cap tray, a sieve tray, a ripple tray, a ballast tray, a valve tray, a counterflow tray, a Unifrax tray, a Superfrac tray, a Maxfrac tray, a dual flow tray, a grid plate tray, a turbogrid plate tray, a Kittel tray, and a high performance tray such as UFM (manufactured by Sulzer Ltd.). In the case where there are stages in the continuous multi-stage distillation column in which the catalyst is not present and hence reaction substantially does not take place (e.g., stages above the stage at which the catalyst is introduced), a distillation column in which these stages are packed with packing, i.e., a multi-stage distillation column having both a tray portion and a portion packed with the packing, is also preferable. Examples of such packing include a random packing such as a Raschig ring, a Lessing ring, a Pall ring, a Berl saddle, an Intalox saddle, a Dixon packing, a McMahon packing or Heli-Pak, or a structured packing such as Mellapak, Gempak, Techno-pack, Flexipac, a Sulzer packing, a Goodroll packing or Glitschgrid. The term "the number of stages n" used in the present embodiment means the number of trays in the case of the tray, and the theoretical number of stages in the case of the packing. The number of stages n in the case of a multi-stage distillation column having both a tray portion and a portion packed with the packing is thus the sum of the number of trays and the theoretical number of stages.

In the production method of the present embodiment, high reactivity, high selectivity, and high productivity can be attained using n stages of any of the above trays, where sieve trays each having a sieve portion (a tray deck portion) and a downcomer portion are particularly preferable as the trays in terms of the relationship between performance and equipment cost. It is also preferable that each sieve tray preferably has 100 to 1,000 holes/m 2 in the sieve portion. A more preferable number of holes is 120 to 900 holes/$m^2$, further preferably 150 to 800 holes/$m^2$. Moreover, the cross-sectional area per hole of each sieve tray is preferably 0.5 to 5 $cm^2$. A more preferable cross-sectional area per hole is 0.7 to 4 $cm^2$, more preferably 0.9 to 3 $cm^2$. Furthermore, it is particularly preferable when each sieve tray has 100 to 1,000 holes/m 2 in the sieve portion, and the cross-sectional area per hole is 0.5 to 5 $cm^2$. The number of holes in the sieve portion may be the same for all of the sieve trays, or may differ, as long as the number of holes in the sieve portion meets the requirements of (7) and (8) above.

FIG. 2 shows a conceptual diagram of an example of a tray structure in the continuous multi-stage distillation column used in the present embodiment. As shown in FIG. 2, the tray in the distillation column has a downcomer portion 11 and a tray deck portion 13. A compartment with holes 14 (portions shown by small circles represent each hole in FIG. 2) in the tray deck portion 13 (compartment ranging from a boundary 15 of the minimum segment including all holes to 4 inches further outward) is an active area 12. During distillation, liquid and steam actually come into contact in the active area 12, and the liquid foamed on the tray deck portion 13 is divided into liquid and steam in the downcomer portion 11, and only the liquid is sent to a lower stage.

The percentage of the active area in each stage tray used in the present embodiment is calculated by the following Formula (i).

$$\text{Percentage (\%) of active area} = \text{area } (cm^2) \text{ of active area/area } (cm^2) \text{ of tray} \times 100 \quad \text{(i)}$$

wherein, the area of active area is an area of the compartment with a hole in the tray deck portion (ranging from the boundary of the minimum segment including all holes to 4 inches further outward), and the area of tray is an area of the tray deck portion, including the area of active area, but not including the downcomer portion.

Furthermore, the percentage of open area in each stage tray used in the present embodiment is calculated by the following Formula (ii).

$$\text{Percentage (\%) of open area} = \text{area } (cm^2) \text{ of open area/area } (cm^2) \text{ of active area} \times 100 \quad \text{(ii)}$$

wherein, the area of open area is the total area of all holes in the active area, and the area of active area is as defined in Formula (i).

In each stage tray of the upper and middle stages used in the present embodiment, the percentage (%) of active area calculated by Formula (i) above is 40 to 80%, preferably 40 to 70%, further preferably 45 to 65%, particularly preferably 45 to 55%. In each stage tray of the lower stage used in the present embodiment, the percentage (%) of the active area calculated by Formula (i) above is 40 to 80%, preferably 40 to 70%, further preferably 45 to 65%, particularly preferably 45 to 55%. In each stage tray of the lower stage used in the present embodiment, the percentage (%) of open area calculated by Formula (ii) above is 1.0 to 5.0%, preferably 1.0 to 4.0%, further preferably 2.0 to 3.5%. In each stage tray of the upper and middle stages used in the present embodiment, the percentage (%) of open area calculated by Formula (ii) above is 1.0 times or more, preferably 1.0 to 6.0 times, more preferably 1.0 to 3.0 times, further preferably 1.0 to 1.5 times the percentage of open area calculated by Formula (ii) above in each stage tray of the lower stage.

By setting the percentages of active area and open area to be not less than the lower limit value in each stage tray in the upper, middle, and lower stages, the differential pressure in the column decreases, the processing capacity is improved, the reaction progresses sufficiently, the yield is improved, and the amount produced is improved. By setting the percentages of active area and open area to be not more than the upper limit value in each stage tray in the upper, middle, and lower stages, the separation of the reaction products becomes sufficient, the product purity is improved, the reaction progresses sufficiently, the yield is improved, and the amount produced is improved.

When carrying out the production method of the present embodiment, it is preferable to control the gas flow rate and the liquid flow rate in each of the upper stage, the middle stage, and the lower stage.

In the upper stage used in the present embodiment, the gas flow rate (kg/hr) is preferably 5,000 to 45,000 kg/hr, more preferably 10,000 to 25,000 kg/hr, and further preferably 15,000 to 25,000 kg/hr.

In the middle stage used in the present embodiment, the gas flow rate (kg/hr) is preferably 5,000 to 30,000 kg/hr, more preferably 10,000 to 25,000 kg/hr, and further preferably 10,000 to 20,000 kg/hr.

In the lower stage used in the present embodiment, the gas flow rate (kg/hr) is preferably 5,000 to 20,000 kg/hr, and more preferably 5,000 to 10,000 kg/hr.

In the upper stage used in the present embodiment, the liquid flow rate (kg/hr) is preferably 1,000 to 15,000 kg/hr, more preferably 3,000 to 10,000 kg/hr, and further preferably 4,000 to 8,000 kg/hr.

In the middle stage used in the present embodiment, the liquid flow rate (kg/hr) is preferably 1,000 to 15,000 kg/hr, more preferably 3,000 to 10,000 kg/hr, and further preferably 3,000 to 8,000 kg/hr.

In the lower stage used in the present embodiment, the liquid flow rate (kg/hr) is preferably 1,000 to 30,000 kg/hr, more preferably 5,000 to 20,000 kg/hr, and further preferably 5,000 to 15,000 kg/hr.

When the gas flow rate and liquid flow rate of each of the upper stage, middle stage, and lower stage used in the present embodiment are set to be not less than the lower limit value, the separation of the reaction products becomes sufficient, the product purity is improved, the reaction progresses sufficiently, the yield is improved, and the amount produced is improved. In addition, when the gas flow rate and liquid flow rate of each of the upper, middle, and lower stages used in the present embodiment are set to be not more than the upper limit value, the differential pressure in the column is reduced, the processing capacity is improved, the reaction progresses sufficiently, the yield is improved, and the amount produced is improved.

By adding the above conditions to the continuous multi-stage distillation column, the object of the present invention can be attained more easily.

When carrying out the production method of the present embodiment, the dialkyl carbonate and the diol are continuously produced by continuously feeding the cyclic carbonate and the aliphatic monohydric alcohol as the starting materials into the continuous multi-stage distillation column in which the catalyst is present, carrying out reaction and distillation simultaneously in the column, continuously withdrawing a low boiling point reaction mixture containing the produced dialkyl carbonate from the upper portion of the column in a gaseous form, and continuously withdrawing a high boiling point reaction mixture containing the diol in a liquid form from the lower portion of the column.

The reaction time for the transesterification reaction carried out in the production method of the present embodiment is considered to equate to the average residence time of the reaction liquid in the continuous multi-stage distillation column. The reaction time varies depending on the shape of the internals in the distillation column and the number of stages, the amounts of the starting materials fed, the type and amount of the catalyst, the reaction conditions, and the like, but is preferably 0.1 to 20 hours, more preferably 0.5 to 15 hours, and further preferably 1 to 10 hours.

The reaction temperature for the transesterification reaction carried out in the production method of the present embodiment varies depending on the type of starting material compounds used, and the type and amount of the catalyst, but is preferably 30 to 300° C. It is preferable to increase the reaction temperature so as to increase the reaction rate. However, if the reaction temperature is too high, side reactions become liable to occur. The reaction temperature is thus more preferably in the range of 40 to 250° C., further preferably 50 to 200° C., and particularly preferably 60 to 150° C. In the production method of the present embodiment, the reactive distillation can be carried out with the column bottom temperature set to preferably 150° C. or lower, more preferably 130° C. or lower, further preferably 110° C. or lower, and particularly more preferably 100° C. or lower. An excellent characteristic feature of the present invention is that high reactivity, high selectivity, and high productivity can be attained even with such a low column bottom temperature. Moreover, the reaction pressure for the transesterification reaction carried out in the production method of the present embodiment varies depending on the type and composition of the starting material compounds used, the reaction temperature, and the like. The reaction pressure may be any of a reduced pressure, a normal pressure, or an applied pressure, and is preferably 1 Pa to $2\times10^7$ Pa, more preferably $10^3$ Pa to $10^7$ Pa, and further preferably $10^4$ to $5\times10^6$ Pa.

The material constituting the continuous multi-stage distillation column used in the present embodiment is not particularly limited, but generally a metallic material such as carbon steel or stainless steel. In terms of the quality of the dialkyl carbonates and the diols to be produced, the material is preferably stainless steel.

EXAMPLES

Hereinafter, the present invention is more specifically described by Examples, but the present invention is not limited to the following Examples.

Example 1

<Continuous Multi-Stage Distillation Column>

A continuous multi-stage distillation column (tray column type distillation column) as shown in FIG. 1, having a column length L: 3300 cm, a column inner diameter D: 300 cm, L/D: 11, the number of stages n: 60, the ratio of the inner diameter D of the column to an inner diameter $d_1$ of a gas outlet ($D/d_1$): 7.5, and the ratio of the inner diameter D of the column to an inner diameter $d_2$ of a liquid outlet ($D/d_2$): 12 was used. The trays in the distillation column were sieve trays having a plurality of holes, the trays each having the cross-sectional area per hole in the sieve portion thereof of approximately 1.3 $cm^2$. The structure of the internal (tray) of this distillation column differed in the place where it was installed, and there were three types of tray structures of the upper, middle, and lower stages. The upper stage was a stage above the stage of the inlet of the cyclic carbonate (ethylene carbonate) (the inlet (3-*a*) provided at the 5th stage from the top of the distillation column). The number of trays of the upper stage was 5, which was 8.3% of the total number of stages 60. The percentage of the active area of each stage tray of the upper stage was 45%, and the percentage of open area was 4.5%. The middle stage was a stage at or below the stage of the inlet of the cyclic carbonate (ethylene carbonate) (the inlet (3-*a*) provided at the 5th stage from the top of the distillation column) and at or above the stage of the inlet of the aliphatic monohydric alcohol (methanol) (the inlets (3-*b*) and (3-*c*) provided at the 30th stage from the top of the distillation column). The number of trays of the middle stage was 24, which was 40% of the total number of stages 60. The percentage of active area was 45%, and the percentage of open area was 3.5% in each stage tray of the middle stage. In addition, the lower stage was a stage below the stage of the inlet of the aliphatic monohydric alcohol (methanol) (the inlets (3-*b*) and (3-*c*) provided at the 30th stage from the top of the distillation column). The number of trays of the lower stage was 31, which was 51.7% of the total number of stages 60. The percentage of active area was 45%, and the percentage of open area was 3.0% in each stage tray of the lower stage.

<Reactive Distillation>

In the continuous multi-stage distillation column shown in FIG. 1, ethylene carbonate in a liquid form was continuously introduced at a flow rate of 4.7 ton/hr into the distillation column through the inlet (3-*a*) provided at the 5th stage from the top of the distillation column. Methanol in a gaseous form (containing dimethyl carbonate at 8.8% by mass) was continuously introduced at a flow rate of 4.622 ton/hr into the distillation column through the inlet (3-*b*) provided at the 30th stage from the top of the distillation column, and methanol in a liquid form (containing dimethyl carbonate at 6.5% by mass) was continuously introduced at a flow rate of 10.695 ton/hr into the distillation column through the inlet (3-*c*) provided at the 30th stage from the top of the distillation column.

The catalyst consisted of a mixture of alkali metal and ethylene glycol, wherein the mass ratio of alkali metal to ethylene glycol (alkali metal/ethylene glycol) in the catalyst was in the range of 0.2 to 0.3. The catalyst was a homogeneous catalyst synthesized by adding 4.8 tons of ethylene glycol to 2.5 tons of alkali metal (potassium), heating the mixture to about 130° C., and heat-treating at about 1300 Pa for about 3 hours to make it into a homogeneous solution. This homogeneous catalyst solution was continuously introduced into the distillation column through the inlet (3-*e*) provided at the 54th stage from the bottom of the distillation column (catalyst concentration (in terms of alkali metal concentration): 1.0% by mass of the ethylene carbonate fed). The reactive distillation was carried out continuously under conditions where the temperature at the column bottom portion was 98° C., the pressure at the column top portion was about $1.118\times10^5$ Pa, and the reflux ratio was 0.52.

When carrying out the reactive distillation, the gas flow rate was 19,600 to 23,000 kg/hr, and the liquid flow rate was 6,000 to 7,700 kg/hr in the upper stage of the column; the gas flow rate was 9,250 to 16,000 kg/hr, and the liquid flow rate was 5,800 to 6,500 kg/hr in the middle stage of the column; and the gas flow rate was 5,280 to 10,000 kg/hr, and the liquid flow rate was 7,980 to 14,900 kg/hr in the lower stage of the column.

It was possible to attain stable steady-state operation after 24 hours. A low boiling point reaction mixture withdrawn in a gaseous form through the gas outlet 1 at the column top portion was cooled using a heat exchanger and thus turned into a liquid. In the low-boiling point reaction mixture in a liquid form continuously withdrawn at 15.246 ton/hr from the distillation column, the proportion of dimethyl carbonate was 5.283 ton/hr, and the proportion of methanol was 8.429 ton/hr. In the liquid continuously withdrawn at 4.883 ton/hr through the liquid outlet 2 at the column bottom portion, the proportion of ethylene glycol was 3.027 ton/hr, the proportion of methanol was 1.303 ton/hr, and the proportion of unreacted ethylene carbonate was 7.6 kg/hr. The actual amount produced per hour of dimethyl carbonate excluding dimethyl carbonate contained in the starting material was 4.651 tons, and the actual amount produced per hour of ethylene glycol excluding ethylene glycol contained in the catalyst solution was 2.955 tons. The reactivity of ethylene carbonate was 99.7%, the selectivity of dimethyl carbonate was 99.99% or more, and the selectivity of ethylene glycol was 99.99% or more.

Continuous operation for a prolonged period was carried out under these conditions. After 500 hours, 2,000 hours, 4,000 hours, 5,000 hours, and 6,000 hours of the continuous operation, the actual amount produced per hour of dimethyl carbonate was 4.661 tons, 4.682 tons, 4.661 tons, 4.661 tons, and 4.692 tons, respectively; the actual amount produced per hour of ethylene glycol was 2.982 tons, 2.955 tons, 2.9222 tons, 2.952 tons, and 2.996 tons, respectively; the reactivity of ethylene carbonate was 99.89%, 99.90%, 99.90%, 99.88%, and 99.92%, respectively; the selectivity of dimethyl carbonate was 99.99% or more, 99.99% or more, 99.99% or more, 99.99% or more, and 99.99% or more, respectively; and the selectivity of ethylene glycol was 99.99% or more, 99.99% or more, 99.99% or more, 99.99% or more, and 99.99% or more, respectively.

Example 2

<Continuous Multi-Stage Distillation Column>

Reactive distillation was carried out using the same continuous multi-stage distillation column as in Example 1 except for changing the tray structure as follows. In each stage tray of the upper stage, the percentage of active area was 60%, and the percentage of open area was 5.0%. In each stage tray of the middle stage, the percentage of active area was 60%, and the percentage of open area was 4.0%. In each stage tray of the lower stage, the percentage of active area was 45%, and the percentage of open area was 3.5%.

<Reactive Distillation>

Reactive distillation was carried out continuously under the same conditions as in Example 1 except for the following conditions.

The catalyst was synthesized in the same way as in Example 1 and continuously introduced into the distillation column through the inlet (3-*e*) provided at the 54th stage from the bottom of the distillation column (catalyst concentration (in terms of alkali metal concentration): 0.5% by mass of the ethylene carbonate fed). The reactive distillation was carried out continuously under conditions where the temperature at the column bottom portion was 98° C., the pressure at the column top portion was about $1.118\times10^5$ Pa, and the reflux ratio was 0.6.

When carrying out the reactive distillation, the gas flow rate was 21,200 to 24,500 kg/hr, and the liquid flow rate was 4,730 to 6,250 kg/hr in the upper stage of the column; the gas flow rate was 10,040 to 19,200 kg/hr, and the liquid flow rate was 4,630 to 6,000 kg/hr in the middle stage; and the gas flow rate was 6,170 to 9,490 kg/hr, and the liquid flow rate was 7,200 to 14,100 kg/hr in the lower stage.

After 24 hours, a stable steady operation was attained. The low boiling point reaction mixture withdrawn in a gaseous form through the gas outlet 1 at the column top portion was cooled by a heat exchanger and turned into a liquid. In the low-boiling point reaction mixture in a liquid form withdrawn continuously at 15.246 ton/hr from the distillation column, the proportion of dimethyl carbonate was 5.577 ton/hr and the proportion of methanol was 8.898 ton/hr. In the liquid withdrawn continuously at 4.639 ton/hr through the liquid outlet 2 at the column bottom portion, the proportion of ethylene glycol was 3.200 ton/hr, the proportion of methanol was 1.376 ton/hr, and the proportion of unreacted ethylene carbonate was 5.6 kg/hr. The actual amount produced per hour of dimethyl carbonate excluding dimethyl carbonate contained in the starting material was 4.920 tons, and the actual amount produced per hour of ethylene glycol excluding ethylene glycol contained in the catalyst solution was 3.119 tons. The reactivity of ethylene carbonate was 99.88%, the selectivity of dimethyl carbonate was 99.99% or more, and the selectivity of ethylene glycol was 99.99% or more.

Continuous operation for a prolonged period was carried out under these conditions. After 500 hours, 2,000 hours, 4,000 hours, 5,000 hours, and 6,000 hours of the continuous operation, the actual amount produced per hour of dimethyl carbonate was 4.630 tons, 4.828 tons, 4.639 tons, 4.635 tons, and 4.728 tons, respectively; the actual amount produced per hour of ethylene glycol was 3.222 tons, 3.283 tons, 3.265 tons, 3.226 tons, and 3.232 tons, respectively; the reactivity of ethylene carbonate was 99.99%, 99.99%, 99.99%, 99.99%, and 99.99%, respectively; the selectivity of dimethyl carbonate was 99.99% or more, 99.99% or more, 99.99% or more, 99.99% or more, and 99.99% or more, respectively; and the selectivity of ethylene glycol was 99.99% or more, 99.99% or more, 99.99% or more, 99.99% or more, and 99.99% or more, respectively.

Example 3

<Continuous Multi-Stage Distillation Column>

The reactive distillation was carried out using the same continuous multi-stage distillation column as in Example 1, setting the tray structure to the same state as in Example 1 as follows, and changing the amount of the starting materials introduced into the distillation column.

In each stage tray of the upper stage, the percentage of active area was 45%, and the percentage of open area was 4.5%. In each stage tray of the middle stage, the percentage of active area was 45%, and the percentage of open area was 3.5%. In each stage tray of the lower stage, the percentage of active area was 45%, and the percentage of open area was 3.0%.

In the continuous multi-stage distillation column shown in FIG. 1, ethylene carbonate in a liquid form was continuously introduced at a flow rate of 8.68 ton/hr into the distillation column through the inlet (3-*a*) provided at the 5th stage from the top of the distillation column. Methanol in a gaseous form (containing dimethyl carbonate at 8.8% by mass) was continuously introduced at a flow rate of 8.53 ton/hr into the distillation column through the inlet (3-*b*) provided at the 30th stage from the top of the distillation column, and methanol in a liquid form (containing dimethyl carbonate at 6.5% by mass) was continuously introduced at a flow rate of 19.74 ton/hr into the distillation column through the inlet (3-*c*) provided at the 30th stage from the top of the distillation column.

<Reactive Distillation>

Reactive distillation was carried out continuously under the same conditions as in Example 1 except for the following conditions.

The catalyst was synthesized in the same way as in Example 1 and continuously introduced into the distillation column through the inlet (3-*e*) provided at the 54th stage from the bottom of the distillation column (catalyst concentration (in terms of alkali metal concentration): 0.6% by mass of the ethylene carbonate fed). The reactive distillation was carried out continuously under conditions where the temperature at the column bottom portion was 98° C., the pressure at the column top portion was about 1.118×10 5 Pa, and the reflux ratio was 0.45.

When carrying out the reactive distillation, the gas flow rate was 36,260 to 42,550 kg/hr, and the liquid flow rate was 11,110 to 14,250 kg/hr in the upper stage of the column; the gas flow rate was 17,110 to 29,600 kg/hr, and the liquid flow rate was 10,730 to 12,030 kg/hr in the middle stage; and the gas flow rate was 9,770 to 18,500 kg/hr, and the liquid flow rate was 14,760 to 27,570 kg/hr in the lower stage.

After 24 hours, a stable steady operation was attained. The low boiling point reaction mixture withdrawn in a gaseous form through the gas outlet 1 at the column top portion was cooled by a heat exchanger and turned into a liquid. In the low-boiling point reaction mixture in a liquid form withdrawn continuously at 28.205 ton/hr from the distillation column, the proportion of dimethyl carbonate was 9.774 ton/hr and the proportion of methanol was 15.594 ton/hr. In the liquid withdrawn continuously at 9.034 ton/hr through the liquid outlet 2 at the column bottom portion, the proportion of ethylene glycol was 5.600 ton/hr, the proportion of methanol was 2.411 ton/hr, and the proportion of unreacted ethylene carbonate was 14.06 kg/hr. The actual amount produced per hour of dimethyl carbonate excluding dimethyl carbonate contained in the starting material was 8.604 tons, and the actual amount produced per hour of ethylene glycol excluding ethylene glycol contained in the catalyst solution was 5.467 tons. The reactivity of ethylene carbonate was 99.88%, the selectivity of dimethyl carbonate was 99.99% or more, and the selectivity of ethylene glycol was 99.99% or more.

Continuous operation for a prolonged period was carried out under these conditions. After 500 hours, 2,000 hours, 4,000 hours, 5,000 hours, and 6,000 hours of the continuous operation, the actual amount produced per hour of dimethyl carbonate was 8.604 tons, 8.604 tons, 8.604 tons, 8.604 tons, and 8.604 tons, respectively; the actual amount produced per hour of ethylene glycol was 5.467 tons, 5.467 tons, 5.467 tons, 5.467 tons, and 5.467 tons, respectively; the reactivity of ethylene carbonate was 99.99%, 99.99%, 99.99%, 99.99%, and 99.99%, respectively; the selectivity of dimethyl carbonate was 99.99% or more, 99.99% or more, 99.99% or more, 99.99% or more, and 99.99% or more, respectively; and the selectivity of ethylene glycol was 99.99% or more, 99.99% or more, 99.99% or more, 99.99% or more, and 99.99% or more, respectively.

Comparative Example 1

<Continuous Multi-Stage Distillation Column>

Reactive distillation was carried out using the same continuous multi-stage distillation column as in Example 1 except for changing the tray structure as follows. In each stage tray of the upper stage, the percentage of active area was 38%, and the percentage of open area was 4.5%. In each stage tray of the middle stage, the percentage of active area was 38%, and the percentage of open area was 4.5%. In each stage tray of the lower stage, the percentage of active area was 38%, and the percentage of open area was 4.8%.

<Reactive Distillation>

Reactive distillation was carried out continuously under the same conditions as in Example 1 except for the following conditions.

In the continuous multi-stage distillation column shown in FIG. 1, ethylene carbonate in a liquid form was continuously introduced into the distillation column through the inlet (3-*a*) provided at the 5th stage from the top of the distillation column at a flow rate of 7.546 ton/hr. Methanol in a gaseous form (containing dimethyl carbonate at 8.8% by mass) was continuously introduced at a flow rate of 7.742 ton/hr into the distillation column through the inlet (3-*b*) provided at the 30th stage from the top of the distillation column, and methanol in a liquid form (containing dimethyl carbonate at 6.5% by mass) was continuously introduced at a flow rate of 17.282 ton/hr into the distillation column through the inlet (3-*c*) provided at the 30th stage from the top of the distillation column.

The catalyst was synthesized in the same way as in Example 1 and continuously introduced into the distillation column through the inlet (3-*e*) provided at the 54th stage from the bottom of the distillation column (catalyst concentration (in terms of alkali metal concentration): 0.6% by mass of the ethylene carbonate fed).

The reactive distillation was carried out continuously under conditions where the temperature at the column bottom portion was 98° C., the pressure at the column top portion was about 1.118×10 5 Pa, and the reflux ratio was 0.45.

When carrying out the reactive distillation, the gas flow rate was 31,523 to 36,991 kg/hr, and the liquid flow rate was 9,906 to 12,384 kg/hr in the upper stage of the column; the gas flow rate was 15,272 to 25,733 kg/hr, and the liquid flow rate was 9,575 to 10,454 kg/hr in the middle stage; and the gas flow rate was 8,717 to 16,083 kg/hr, and the liquid flow rate was 13,174 to 23,964 kg/hr in the lower stage.

After 24 hours, a stable steady operation was attained. The low boiling point reaction mixture withdrawn in a gaseous form through the gas outlet 1 at the column top portion was cooled by a heat exchanger and turned into a liquid. In the low-boiling point reaction mixture in a liquid form withdrawn continuously at 24.642 ton/hr from the distillation column, the proportion of dimethyl carbonate was 4.109 ton/hr and the proportion of methanol was 15.115 ton/hr. In the liquid continuously withdrawn at 7.804 ton/hr through the liquid outlet 2 at the column bottom portion, the proportion of ethylene glycol was 5.436 ton/hr, the proportion of methanol was 2.34 ton/hr, and the proportion of unreacted ethylene carbonate was 14.122 kg/hr. The actual amount produced per hour of dimethyl carbonate excluding dimethyl carbonate contained in the starting material was 7.708 tons, and the actual amount produced per hour of ethylene glycol excluding ethylene glycol contained in the catalyst solution was 5.310 tons. The reactivity of ethylene carbonate was 99.7%, the selectivity of dimethyl carbonate was 99.99% or more, and the selectivity of ethylene glycol was 99.99% or more.

Continuous operation for a prolonged period was carried out under these conditions. After 500 hours, 2,000 hours, 4,000 hours, 5,000 hours, and 6,000 hours of the continuous operation, the actual amount produced per hour of dimethyl carbonate was 7.708 tons, 7.708 tons, 7.706 tons, 7.706 tons, and 7.708 tons, respectively; the actual amount produced per hour of ethylene glycol was 5.310 tons, 5.312 tons, 5.310 tons, 5.310 tons, and 5.310 tons, respectively; the reactivity of ethylene carbonate was 99.7%, 99.7%, 99.7%, 99.7%, and 99.7%, respectively; the selectivity of dimethyl carbonate was 99.99%, 99.99%, 99.99%, 99.99%, and 99.99%, respectively; and the selectivity of ethylene glycol was 99.99%, 99.99%, 99.99%, 99.99%, and 99.99%, respectively.

Comparative Example 2

<Continuous Multi-Stage Distillation Column>

Reactive distillation was carried out continuously under the same conditions as in Example 1 except for the following conditions. The same amounts of starting materials as in Example 3 were continuously introduced into the distillation column.

For the tray structure of the continuous multi-stage distillation column, the percentage of active area was 82%, and the percentage of open area was 4.9% in each stage tray of the upper stage. The percentage of active area was 82%, and the percentage of open area was 4.9% in each stage tray of the middle stage. The percentage of active area was 85%, and the percentage of open area was 3.3% in each stage tray of the lower stage.

In the continuous multi-stage distillation column shown in FIG. 1, ethylene carbonate in a liquid form was continuously introduced at a flow rate of 8.68 ton/hr into the distillation column through the inlet (3-*a*) provided at the 5th stage from the top of the distillation column. Methanol in a gaseous form (containing dimethyl carbonate at 8.8% by mass) was continuously introduced at a flow rate of 8.53 ton/hr into the distillation column through the inlet (3-*b*) provided at the 30th stage from the top of the distillation column, and methanol in a liquid form (containing dimethyl carbonate at 6.5% by mass) was continuously introduced at a flow rate of 19.74 ton/hr into the distillation column through the inlet (3-*c*) provided at the 30th stage from the top of the distillation column.

<Reactive Distillation>

Reactive distillation was carried out continuously under the same conditions as in Example 3.

The catalyst was synthesized in the same way as in Example 1 and continuously introduced into the distillation column through the inlet (3-*e*) provided at the 54th stage from the bottom of the distillation column (catalyst concentration (in terms of alkali metal concentration): 0.6% by mass of the ethylene carbonate fed). The reactive distillation was carried out continuously under conditions where the temperature at the column bottom portion was 98° C., the pressure at the column top portion was about 1.118×10 5 Pa, and the reflux ratio was 0.45.

When carrying out the reactive distillation, the gas flow rate was 33,250 to 40,200 kg/hr, and the liquid flow rate was 12,520 to 40,200 kg/hr in the upper stage of the column; the gas flow rate was 15,420 to 25,200 kg/hr, and the liquid flow rate was 12,320 to 14,250 kg/hr in the middle stage; and the gas flow rate was 8,270 to 14,200 kg/hr, and the liquid flow rate was 13,750 to 24,450 kg/hr in the lower stage.

After 24 hours, a stable steady operation was attained. The low boiling point reaction mixture withdrawn in a gaseous form through the gas outlet 1 at the column top portion was cooled by a heat exchanger and turned into a liquid. In the low-boiling point reaction mixture in a liquid form withdrawn continuously at 28.036 ton/hr from the distillation column, the proportion of dimethyl carbonate was 9.715 ton/hr and the proportion of methanol was 15.550 ton/hr. In the liquid withdrawn continuously at 8.979 ton/hr through the liquid outlet 2 at the column bottom portion, the proportion of ethylene glycol was 5.634 ton/hr, the proportion of methanol was 2.396 ton/hr, and the proportion of unreacted ethylene carbonate was 14.153 kg/hr. The actual amount produced per hour of dimethyl carbonate excluding dimethyl carbonate contained in the starting material was 8.543 tons, and the actual amount produced per hour of ethylene glycol excluding ethylene glycol contained in the catalyst solution was 5.431 tons. The reactivity of ethylene carbonate was 99.33%, the selectivity of dimethyl carbonate was 99.33%, and the selectivity of ethylene glycol was 99.33%.

Continuous operation for a prolonged period was carried out under these conditions. After 500 hours, 1,000 hours, and 2,000 hours of the continuous operation, the actual amount produced per hour of dimethyl carbonate was 8.547 tons, 8.547 tons, and 8.546 tons, respectively; the actual amount produced per hour of ethylene glycol was 5.431 tons, 5.430 tons, 5.431 tons, respectively; the reactivity of ethylene carbonate was 99.33%, 99.33%, and 99.32%, respectively; the selectivity of dimethyl carbonate was 99.43%, 99.43%, and 99.53%, respectively; and the selectivity of ethylene glycol was 99.43%, 99.43%, and 99.43%, respectively.

Comparative Example 3

<Continuous Multi-Stage Distillation Column>

Reactive distillation was carried out continuously under the same conditions as in Example 1 except for the following conditions. The same amounts of starting materials as in Comparative Example 1 were continuously introduced into the distillation column.

For the tray structure of the continuous multi-stage distillation column, the percentage of active area was 82% and the percentage of open area was 4.9% in each stage tray of the upper stage. The percentage of active area was 82%, and the percentage of open area was 4.9% in each stage tray of the middle stage. The percentage of active area was 85%, and the percentage of open area was 3.3% in each stage tray of the lower stage.

In the continuous multi-stage distillation column shown in FIG. 1, ethylene carbonate in a liquid form was continuously introduced into the distillation column through the inlet (3-*a*) provided at the 5th stage from the top of the distillation column at a flow rate of 7.546 ton/hr. Methanol in a gaseous form (containing dimethyl carbonate at 8.8% by mass) was continuously introduced at a flow rate of 7.742 ton/hr into the distillation column through the inlet (3-*b*) provided at the 30th stage from the top of the distillation column, and methanol in a liquid form (containing dimethyl carbonate at 6.5% by mass) was continuously introduced at a flow rate of 17.282 ton/hr into the distillation column through the inlet (3-*c*) provided at the 30th stage from the top of the distillation column.

<Reactive Distillation>

Reactive distillation was carried out continuously under the same conditions as in Comparative Example 1.

The catalyst was synthesized in the same way as in Example 1 and continuously introduced into the distillation column through the inlet (3-*e*) provided at the 54th stage from the bottom of the distillation column (catalyst concentration (in terms of alkali metal concentration): 0.6% by mass of the ethylene carbonate fed). The reactive distillation was carried out continuously under conditions where the temperature at the column bottom portion was 98° C., the pressure at the column top portion was about $1.118\times10^5$ Pa, and the reflux ratio was 0.45.

When carrying out the reactive distillation, the gas flow rate was 31,544 to 36,975 kg/hr, and the liquid flow rate was 9,912 to 12,384 kg/hr in the upper stage of the column; the gas flow rate was 15,274 to 25,733 kg/hr, and the liquid flow rate was 9,572 to 10,448 kg/hr in the middle stage; and the gas flow rate was 8,720 to 16,078 kg/hr, and the liquid flow rate was 13,180 to 23,928 kg/hr in the lower stage.

After 24 hours, a stable steady operation was attained. The low boiling point reaction mixture withdrawn in a gaseous form through the gas outlet 1 at the column top portion was cooled by a heat exchanger and turned into a liquid. In the low-boiling point reaction mixture in a liquid form withdrawn continuously at 26.669 ton/hr from the distillation column, the proportion of dimethyl carbonate was 4.113 ton/hr and the proportion of methanol was 15.130 ton/hr. In the liquid withdrawn continuously at 7.796 ton/hr through the liquid outlet 2 at the column bottom portion, the proportion of ethylene glycol was 5.441 ton/hr, the proportion of methanol was 2.338 ton/hr, and the proportion of unreacted ethylene carbonate was 14.082 kg/hr. The actual amount produced per hour of dimethyl carbonate excluding dimethyl carbonate contained in the starting material was 7.716 tons, and the actual amount produced per hour of ethylene glycol excluding ethylene glycol contained in the catalyst solution was 5.315 tons. The reactivity of ethylene carbonate was 99.80%, the selectivity of dimethyl carbonate was 99.89%, and the selectivity of ethylene glycol was 99.90%.

Continuous operation for a prolonged period was carried out under these conditions. After 500 hours, 1,000 hours, and 2,000 hours of the continuous operation, the actual amount produced per hour of dimethyl carbonate was 7.716 tons, 7.716 tons, and 7.716 tons, respectively; the actual amount produced per hour of ethylene glycol was 5.315 tons, 5.315 tons, 5.315 tons, respectively; the reactivity of ethylene carbonate was 99.80%, 99.80%, and 99.80%, respectively; the selectivity of dimethyl carbonate was 99.90%, 99.90%, and 99.90%, respectively; and the selectivity of ethylene glycol was 99.90%, 99.89%, and 99.90%, respectively.

This application is based on Japanese Patent Application No. 2021-002028, filed on Jan. 8, 2021, the contents of which are incorporated herein by reference.

INDUSTRIAL APPLICABILITY

According to the present invention, a dialkyl carbonate and a diol can be produced each with high selectivity of 97% or more, preferably 99% or more, more preferably 99.99% or more, on an industrial scale of 4.5 tons or more per hour, preferably 5 tons or more per hour, more preferably 5.2 tons or more per hour for the dialkyl carbonate, and 2.5 tons or more per hour, preferably 3.0 tons or more per hour, more preferably 3.2 tons or more per hour for the diol, for a prolonged period of 1,000 hours or more, preferably 3,000 hours or more, more preferably 5,000 hours or more, stably with a high yield, from a cyclic carbonate and an aliphatic monohydric alcohol, showing the industrial applicability of the present invention. The upper limit of the amount of dialkyl carbonate produced is not particularly limited, but, for example, 12 tons or less per hour. The upper limit of the amount of diol produced is not particularly limited either, but, for example, 8 tons or less per hour.

REFERENCE SIGNS LIST

1: gas outlet, 2: liquid outlet, 3-*a* to 3-*e*: inlet, 4-*a* to 4-*b*: inlet, 5: end plate, 6: internal, 7: trunk portion, 10: continuous multi-stage distillation column, L: length (cm) of trunk portion, D: inner diameter (cm) of trunk portion, $d_1$: inner diameter (cm) of gas outlet, $d_2$: inner diameter (cm) of liquid outlet, 11: downcomer portion, 12: active area, 13: tray deck portion, 14: one of holes (the portion indicated by a small circle is a hole, and the total area of the holes is an open area), 15: boundary of the minimum segment including all holes

The invention claimed is:

1. A method for industrially producing a dialkyl carbonate and a diol in which the dialkyl carbonate and the diol are continuously produced through a reactive distillation system of taking a cyclic carbonate and an aliphatic monohydric alcohol as starting materials, comprising:

continuously feeding the starting materials into a continuous multi-stage distillation column in which a homogeneous catalyst is present;

carrying out reaction and distillation simultaneously in the column;

continuously withdrawing a low boiling point reaction mixture containing the produced dialkyl carbonate in a gaseous form from an upper portion of the column; and continuously withdrawing a high boiling point reaction mixture containing the diol in a liquid form from a lower portion of the column, wherein:

(a) the continuous multi-stage distillation column comprises a tray column type distillation column which has a structure having a cylindrical trunk portion having a length L (cm) and an inner diameter D (cm) and having an internal therein, the internal being a tray having a plurality of holes, and the column further has a gas outlet at a column top portion or in the upper portion of the column near to the column top portion, a liquid outlet at a column bottom portion or in the lower portion of the column near to the column bottom portion, one or more first inlets provided in the upper portion and/or a middle portion of the column below the gas outlet, and one or more second inlets provided in the middle portion and/or the lower portion of the column above the liquid outlet, wherein:

(1) the length L (cm) of the column satisfies Formula (1):

$$1{,}500 \leq L \leq 12{,}000; \tag{1}$$

(2) the inner diameter D (cm) of the column satisfies Formula (2):

$$120 \leq D \leq 3{,}000; \tag{2}$$

(3) the internal consists of three types of trays of upper, middle, and lower stages;

(4) the starting material cyclic carbonate is continuously introduced into the continuous multi-stage distillation column through the one or more first inlets, and the upper stage is a stage above a stage of the inlet of an uppermost stage among the one or more first inlets, and a percentage of the number of trays of the upper stage is 1 to 10% of the total number of stages, (5) the starting material aliphatic monohydric alcohol is continuously introduced into the continuous multi-stage distillation column through the one or more second inlets, and the middle stage is a stage from a stage of the inlet of an uppermost stage among the one or more second inlets to the stage of the inlet of the uppermost stage among the one or more first inlets, and a percentage of the number of trays of the middle stage is 40 to 50% of the total number of stages;

(6) the lower stage is a stage below the stage of the inlet of the uppermost stage among the one or more second inlets, and a percentage of the number of trays of the lower stage is 45 to 55% of the total number of stages;

(7) in each stage tray of the lower stage, a percentage of active area calculated by Formula (i) below is 40 to 80%, and a percentage of open area calculated by Formula (ii) below is 1.0 to 5.0%:

$$\text{Percentage (\%) of active area} = \text{area}\left(\text{cm}^2\right)\text{ of active area/area}\left(\text{cm}^2\right)\text{ of tray} \times 100 \tag{i}$$

wherein the area of active area is an area of a compartment with a hole in a tray deck portion (ranging from a boundary of a minimum segment including all holes to 4 inches further outward), and the area of tray is an area of the tray deck portion, including the area of active area, but not including a downcomer portion;

$$\text{Percentage (\%) of open area} = \text{area}\left(\text{cm}^2\right)\text{ of open area/area}\left(\text{cm}^2\right)\text{ of active area} \times 100 \tag{ii}$$

wherein the area of open area is the total area of all holes in the active area, and the area of active area is as defined in Formula (i);

(8) in each stage tray of the upper and middle stages, the percentage of active area calculated by Formula (i) above is 40 to 80%, and the percentage of open area calculated by Formula (ii) above is 1.0 times or more the percentage of open area calculated by Formula (ii) above in each stage tray of the lower stage; and (9) the homogeneous catalyst consists of a mixture of an alkali metal and ethylene glycol, and a mass ratio of the alkali metal to the ethylene glycol (alkali metal/ethylene glycol) in the homogeneous catalyst is 0.05 to 0.5, and a catalyst concentration (in terms of alkali metal concentration) is 0.05 to 2.0% by mass of the cyclic carbonate fed to the distillation column.

2. The method according to claim 1, wherein in the upper stage, a gas flow rate is 5,000 to 45,000 kg/hr, and a liquid flow rate is 1,000 to 15,000 kg/hr, in the middle stage, the gas flow rate is 5,000 to 30,000 kg/hr, and the liquid flow rate is 1,000 to 15,000 kg/hr, and in the lower stage, the gas flow rate is 5,000 to 20,000 kg/hr, and the liquid flow rate is 1,000 to 30,000 kg/hr.

3. The method according to claim 1, wherein an amount of the dialkyl carbonate produced is 4.5 tons or more per hour.

4. The method according to claim 1, wherein an amount of the diol produced is 2.5 tons or more per hour.

5. A continuous multi-stage distillation column for carrying out transesterification reaction between a cyclic carbonate and an aliphatic monohydric alcohol and distillation, wherein (a) the continuous multi-stage distillation column comprises:

a cylindrical trunk portion having a length L (cm) and an inner diameter D (cm);

a tray having a plurality of holes, provided inside the trunk portion as an internal;

a gas outlet provided at a column top portion or in an upper portion of the column near to the column top portion;

a liquid outlet provided at a column bottom portion or in a lower portion of the column near to the column bottom portion;

one or more first inlets provided in the upper portion and/or a middle portion of the column below the gas outlet; and one or more second inlets provided in the middle portion and/or the lower portion of the column above the liquid outlet;

(1) the length L (cm) of the column satisfies Formula (1):

$$1{,}500 \leq L \leq 12{,}000; \quad (1)$$

(2) the inner diameter D (cm) of the column satisfies Formula (2):

$$120 \leq D \leq 3{,}000; \quad (2)$$

(3) the internal consists of three types of trays of upper, middle, and lower stages;

(4) the starting material cyclic carbonate is continuously introduced into the continuous multi-stage distillation column through the one or more first inlets, and the upper stage is a stage above a stage of the inlet of an uppermost stage among the one or more first inlets, and a percentage of the number of trays of the upper stage is 1 to 10% of the total number of stages, (5) the starting material aliphatic monohydric alcohol is continuously introduced into the continuous multi-stage distillation column through the one or more second inlets, and the middle stage is a stage from a stage of the inlet of an uppermost stage among the one or more second inlets to the stage of the inlet of the uppermost stage among the one or more first inlets, and a percentage of the number of trays of the middle stage is 40 to 50% of the total number of stages;

(6) the lower stage is a stage below the stage of the inlet of the uppermost stage among the one or more second inlets, and a percentage of the number of trays of the lower stage is 45 to 55% of the total number of stages;

(7) in each stage tray of the lower stage, a percentage of active area calculated by Formula (i) below is 40 to 80%, and a percentage of open area calculated by Formula (ii) below is 1.0 to 5.0%:

$$\text{Percentage (\%) of active area} = \text{area } (\text{cm}^2) \text{ of active area/area } (\text{cm}^2) \text{ of tray} \times 100 \quad (i)$$

wherein the area of active area is an area of a compartment with a hole in a tray deck portion (ranging from a boundary of a minimum segment including all holes to 4 inches further outward), and the area of tray is an area of the tray deck portion, including the area of active area, but not including a downcomer portion;

$$\text{Percentage (\%) of open area} = \text{area } (\text{cm}^2) \text{ of open area/area } (\text{cm}^2) \text{ of active area} \times 100 \quad (ii)$$

wherein the area of open area is the total area of all holes in the active area, and the area of active area is as defined in Formula (i); and (8) in each stage tray of the upper and middle stages, the percentage of active area calculated by Formula (i) above is 40 to 80%, and the percentage of open area calculated by Formula (ii) above is 1.0 times or more the percentage of open area calculated by Formula (ii) above in each stage tray of the lower stage.

6. The method according to claim 2, wherein an amount of the dialkyl carbonate produced is 4.5 tons or more per hour.

7. The method according to claim 2, wherein an amount of the diol produced is 2.5 tons or more per hour.

8. The method according to claim 3, wherein an amount of the diol produced is 2.5 tons or more per hour.

9. The method according to claim 6, wherein an amount of the diol produced is 2.5 tons or more per hour.

* * * * *